(12) United States Patent
Servansky et al.

(10) Patent No.: US 12,642,934 B2
(45) Date of Patent: *Jun. 2, 2026

(54) NON-INVASIVE VENTILATION VIA AN AIR ENTRAINMENT PATIENT INTERFACE

(71) Applicant: KONINKLIJKE PHILIPS N.V., Eindhoven (NL)

(72) Inventors: Daniel Paul Servansky, Pittsburgh, PA (US); Peter Hermanus Bouma, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 584 days.

This patent is subject to a terminal disclaimer.

(21) Appl. No.: 18/214,587

(22) Filed: Jun. 27, 2023

(65) Prior Publication Data

US 2024/0173507 A1     May 30, 2024

Related U.S. Application Data

(60) Provisional application No. 63/428,221, filed on Nov. 28, 2022.

(51) Int. Cl.
| | |
|---|---|
| *A61M 16/06* | (2006.01) |
| *A61M 16/00* | (2006.01) |
| *A61M 16/12* | (2006.01) |

(52) U.S. Cl.
CPC .... *A61M 16/0672* (2014.02); *A61M 16/0003* (2014.02); *A61M 16/0683* (2013.01); *A61M 16/12* (2013.01); *A61M 2016/0027* (2013.01)

(58) Field of Classification Search
CPC .......... A61M 16/0672; A61M 16/0003; A61M 16/0683; A61M 16/12; A61M 2016/0027;

(Continued)

(56) References Cited

U.S. PATENT DOCUMENTS

| | | |
|---|---|---|
| 9,132,250 B2 | 9/2015 | Allum |
| 10,384,028 B2 | 8/2019 | Allum |

(Continued)

FOREIGN PATENT DOCUMENTS

| | | |
|---|---|---|
| WO | 2022040257 A1 | 2/2022 |

OTHER PUBLICATIONS https://www.inogen.com/products/tav-tidal-assist-ventilator/.

(Continued)

*Primary Examiner* — Victoria Murphy
(74) *Attorney, Agent, or Firm* — Daniel H. Brean

(57)     ABSTRACT

An embodiment provides a system having a non-invasive ventilation patient interface. In one example, the system includes a headgear element and a non-invasive ventilation patient interface detachably coupled to the headgear element. The non-invasive ventilation patient interface includes a conduit having an entrainment opening and a nasal opening disposed along a conduit axis. A pressure sensing element is provided proximate to the nasal opening. One or more orifices proximate to the entrainment opening are configured to expel a jet of gas. One or more surfaces have a first end and a second end, with the first end being proximate to the one or more orifices and directing a flow of the jet of gas expelled from the one or more orifices, the second end being closer to the nasal opening than the first end. In an operational state, the jet of gas adheres to the one or more surfaces via the Coanda effect, thereby entraining ambient air into the entrainment opening to deliver the jet of gas and the ambient air through the nasal opening of the conduit.

15 Claims, 11 Drawing Sheets

(58) Field of Classification Search
CPC ........ A61M 16/024; A61M 2202/0208; A61M
2202/0275; A61M 16/0858; A61M
16/127; A61M 16/0666
USPC .................................................... 128/204.24
See application file for complete search history.

(56) References Cited

U.S. PATENT DOCUMENTS

| | | | | |
|---|---|---|---|---|
| 11,154,672 | B2 | 10/2021 | Allum | |
| 11,376,387 | B2 | 7/2022 | Allum | |
| 2010/0252041 | A1 * | 10/2010 | Kapust | A61M 16/0096 |
| | | | | 128/204.23 |
| 2017/0072159 | A1 | 3/2017 | Romano | |
| 2021/0016031 | A1 | 1/2021 | Spence | |

OTHER PUBLICATIONS https://www.hillrom.com/en/products/life-2000-acute-care/.

Britannica, T. E. Jul. 23, 2021). Encyclopedia Britannica. Retrieved Jul. 15, 2022, from https://www.britannica.com/science/Newtons-laws-of-motion.

Merriam-Webster. (n.d.). Merriam-Webster.com dictionary. Retrieved Jul. 21, 2021, from https://www.merriam-webster.com/dictionary/Coandă%20effect.

Raskin, J. Feb. 2003). "Coandă Effect: Understanding Why Wings Work." Retrieved Jul. 15, 2022, from https://www.karmak.org/archive/2003/02/Coandă_effect.htm.

Reba, I. (1966). Applications of the Coandă Effect. Scientific American, (1966).

International Search Report for PCT/EP2023/083381 filed Nov. 28, 2023.

* cited by examiner

405a

403d

410d

405b

Circumferential

Multiple Linear
Slots

Multiple Stacked
Slots

Multiple Vertical
Slots

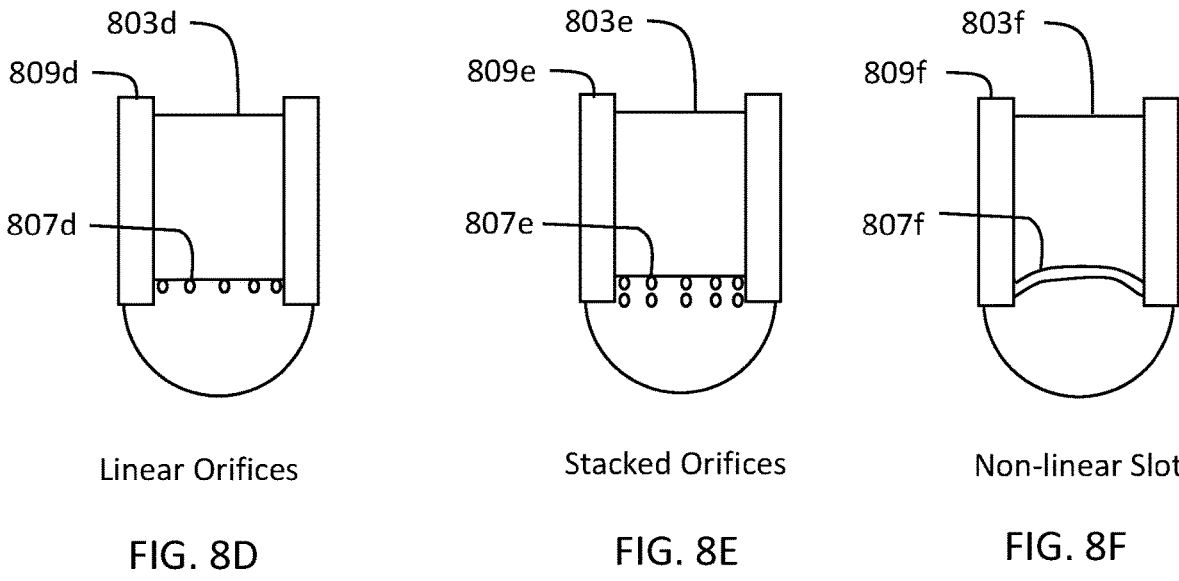
803d
809d
807d
Linear Orifices
FIG. 8D
803e
809e
807e
Stacked Orifices
FIG. 8E
803f
809f
807f
Non-linear Slot
FIG. 8F
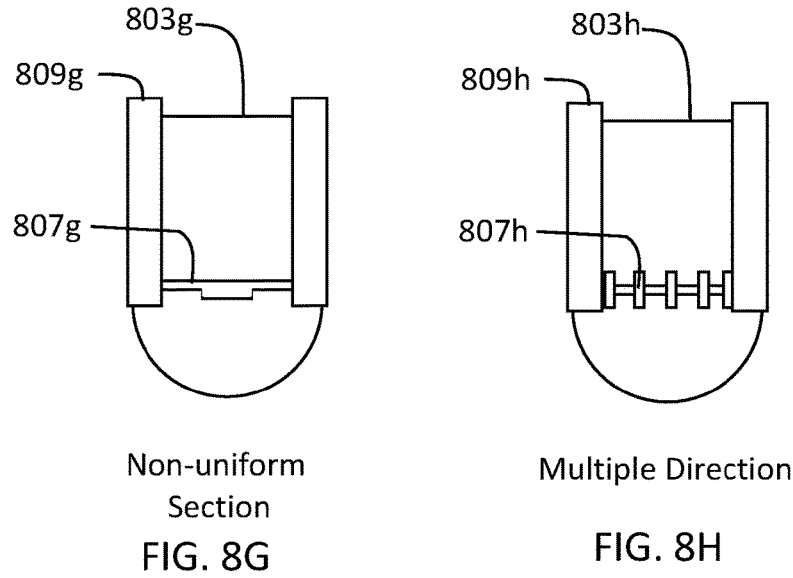
803g
809g
807g
Non-uniform
Section
FIG. 8G
803h
809h
807h
Multiple Direction
FIG. 8H

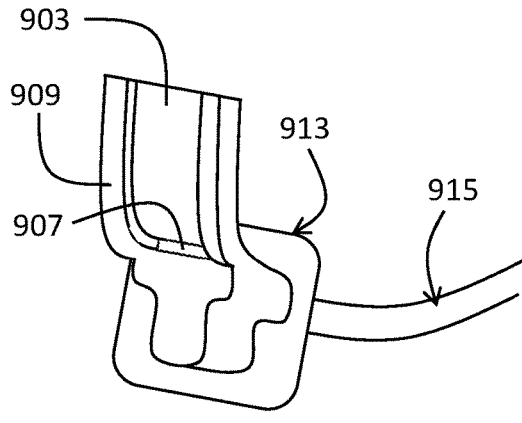
FIG. 9
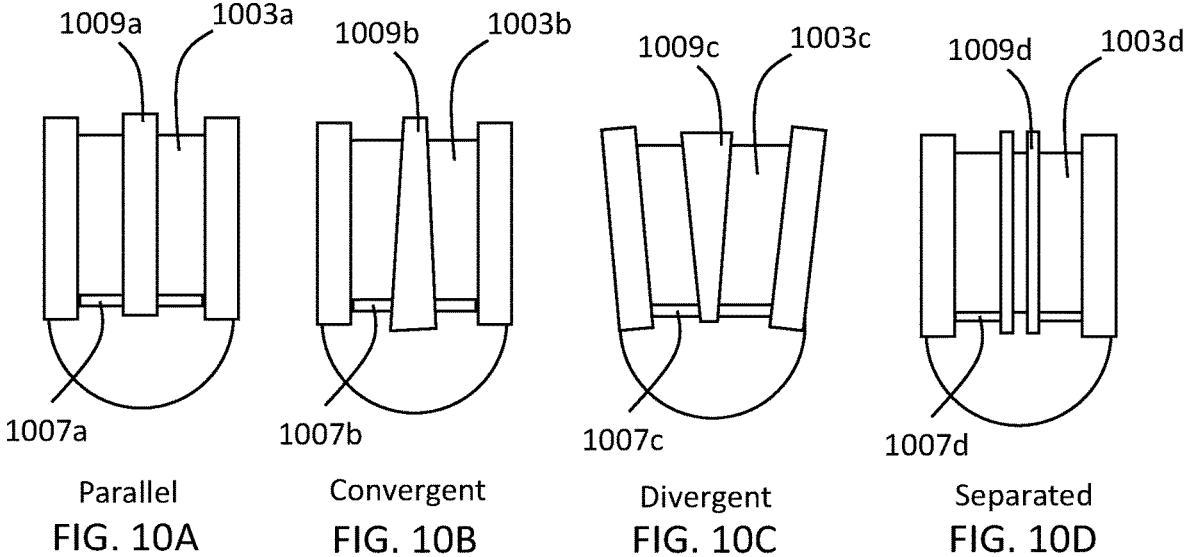
Parallel
FIG. 10A
Convergent
FIG. 10B
Divergent
FIG. 10C
Separated
FIG. 10D
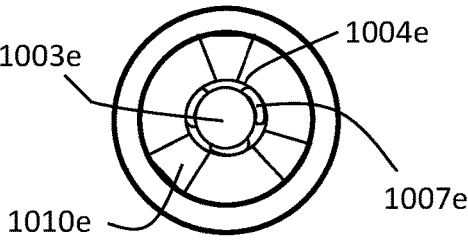
Circumferential
FIG. 10E

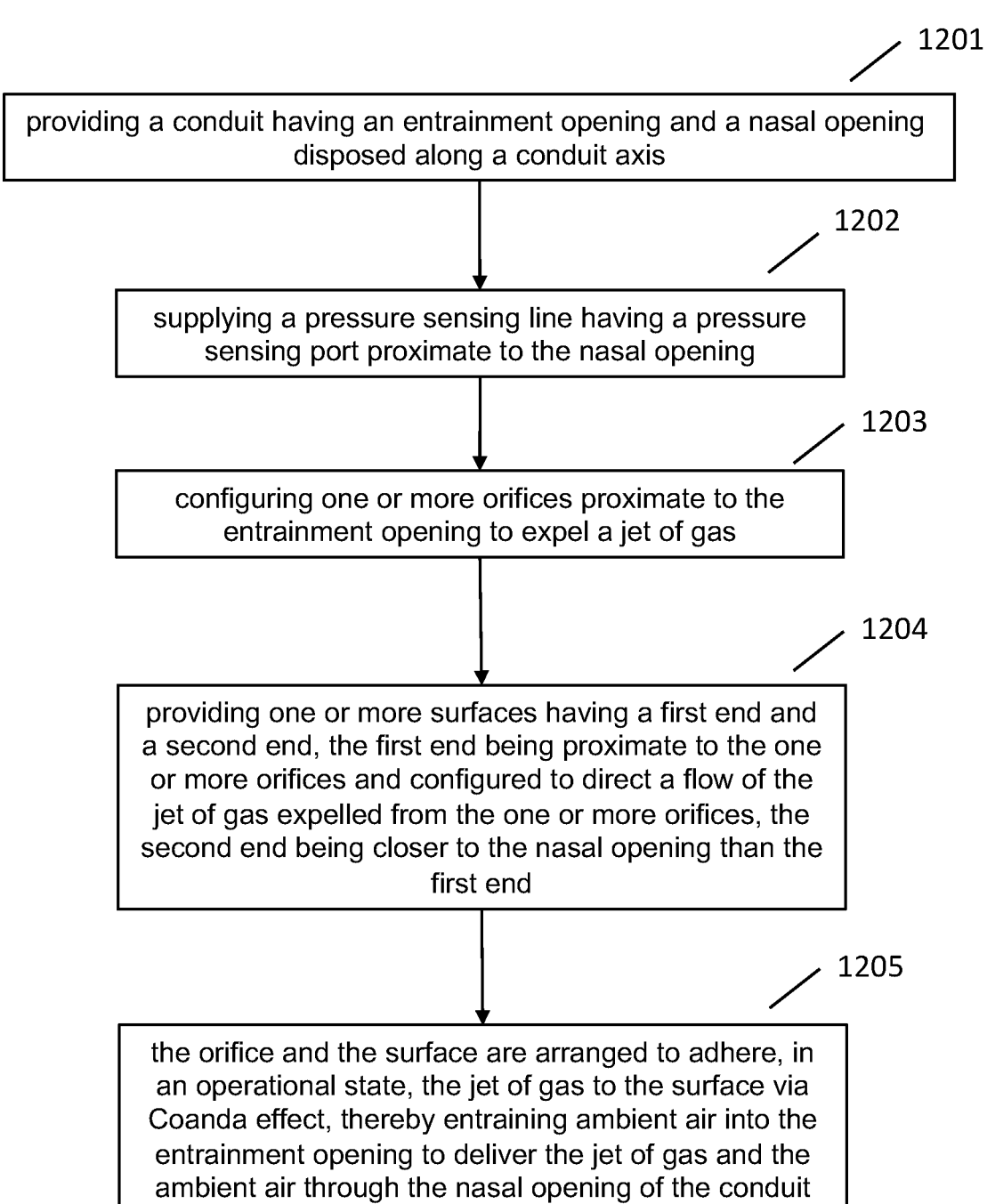

1201 providing a conduit having an entrainment opening and a nasal opening disposed along a conduit axis

1202 supplying a pressure sensing line having a pressure sensing port proximate to the nasal opening

1203 configuring one or more orifices proximate to the entrainment opening to expel a jet of gas

1204 providing one or more surfaces having a first end and a second end, the first end being proximate to the one or more orifices and configured to direct a flow of the jet of gas expelled from the one or more orifices, the second end being closer to the nasal opening than the first end

1205 the orifice and the surface are arranged to adhere, in an operational state, the jet of gas to the surface via Coanda effect, thereby entraining ambient air into the entrainment opening to deliver the jet of gas and the ambient air through the nasal opening of the conduit

FIG. 12

NON-INVASIVE VENTILATION VIA AN AIR ENTRAINMENT PATIENT INTERFACE

CROSS-REFERENCE TO RELATED APPLICATIONS

This patent application claims the priority benefit under 35 U.S.C. § 119(e) of U.S. Provisional Application No. 63/428,221, filed on Nov. 28, 2022, the contents of which are herein incorporated by reference.

1. FIELD OF THE INVENTION

The disclosed subject matter generally pertains to patient ventilation interfaces. Certain disclosed subject matter relates to technologies for non-invasive ventilation via an internal nasal patient entrainment interface.

2. DESCRIPTION OF THE RELATED ART

There are known solutions capable of providing ambulatory non-invasive ventilation. For example, the TIDAL ASSIST ventilator (TAV) of Inogen, Inc. is a handheld controller that connects to a high-pressure oxygen cylinder as the gas source. The TAV can deliver continuous flow oxygen, pulse dose oxygen, or ventilate via a tidal assist mode. In tidal assist mode the controller delivers 50 to 250 mL oxygen pulses into a custom air entrainment patient interface at flows and pressures that create non-invasive inspiratory positive airway pressure (IPAP) in the user's airways. The patient interface utilizes the Venturi principle to entrain air into the pulse of oxygen, creating a larger flow and bolus delivered to the patient, which subsequently creates positive inspiratory pressure (IPAP) as the velocity of the gas slows upon entering the patient's airways. TIDAL ASSIST and TAV are registered trademarks of Inogen, Inc. in the United States and/or other countries.

As another example, the LIFE2000 ventilator of Breathe Technologies, Inc. can also be used while connected to a high-pressure oxygen cylinder but has two other configurations where it can be used, i.e., while either tethered to or docked into an air compressor base station. The LIFE2000 ventilator can provide IPAP and expiratory positive airway pressure (EPAP) from the oxygen cylinder gas source or using air from the compressor base station. LIFE2000 is a registered trademark of Breathe Technologies, Inc. in the United States and/or other countries.

Such known non-invasive nasal patient ventilation interfaces utilize a substantially enclosed configuration whereby a jet of gas entrains ambient air via a port via the Bernoulli principle. This requires a closed structure and results in a large production of noise.

SUMMARY OF THE INVENTION

An embodiment provides a system having a non-invasive ventilation patient interface. In one example, the system includes a headgear element and a non-invasive ventilation patient interface detachably coupled to the headgear element. The non-invasive ventilation patient interface includes a conduit having an entrainment opening and a nasal opening disposed along a conduit axis. A pressure sensing element is provided proximate to the nasal opening. One or more orifices proximate to the entrainment opening are configured to expel a jet of gas. One or more surfaces have a first end and a second end, with the first end being proximate to the one or more orifices and directing a flow of the jet of gas expelled from the one or more orifices, the second end being closer to the nasal opening than the first end. In an operational state, the jet of gas adheres to the one or more surfaces via the Coanda effect, thereby entraining ambient air into the entrainment opening to deliver the jet of gas and the ambient air through the nasal opening of the conduit.

Another embodiment includes a system including a headgear means and a non-invasive ventilation patient interface means detachably coupled to the headgear means. The non-invasive ventilation patient interface means comprises a conduit means having an entrainment opening and a nasal opening disposed along a conduit axis, a pressure sensing means proximate to the nasal opening, one or more orifices means proximate to the entrainment opening and configured to expel a jet of gas, and one or more surface means having a first end and a second end, the first end being proximate to the one or more orifice means and directing a flow of the jet of gas expelled from the one or more orifice means, the second end being closer to the nasal opening than the first end. In an operational state, the jet of gas adheres to the one or more surface means via the Coanda effect, thereby entraining ambient air into the entrainment opening to deliver the jet of gas and the ambient air through the nasal opening of the conduit means.

A further embodiment provides a method including providing a conduit having an entrainment opening and a nasal opening disposed along a conduit axis, supplying a pressure sensing element proximate to the nasal opening, configuring one or more orifices proximate to the entrainment opening to expel a jet of gas, and providing one or more surfaces having a first end and a second end, the first end being proximate to the one or more orifices and configured to direct a flow of the jet of gas expelled from the one or more orifices, the second end being closer to the nasal opening than the first end. In an operational state, a patient interface configured according to the method arranges the orifice and the surface to adhere the jet of gas to the surface via Coanda effect, thereby entraining ambient air into the entrainment opening to deliver the jet of gas and the ambient air through the nasal opening of the conduit.

As will become apparent from reviewing this specification, methods, devices, systems, and products are provided for implementing the various embodiments.

The foregoing is a summary and thus may contain simplifications, generalizations, and omissions of detail; consequently, those skilled in the art will appreciate that the summary is illustrative only and is not intended to be in any way limiting.

These and other features and characteristics of the example embodiments, as well as the methods of operation and functions of the related elements of structure and the combination thereof, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention.

BRIEF DESCRIPTION OF THE DRAWINGS

FIG. 9 illustrates a view of an example surface and opening arrangement.

FIG. 10(A-D) illustrates an example sidewall and orifice arrangement.

FIG. 10E illustrates an example orifice arrangement.

FIG. 12 illustrates an example method.

DETAILED DESCRIPTION OF EXEMPLARY EMBODIMENTS

Figure 1:
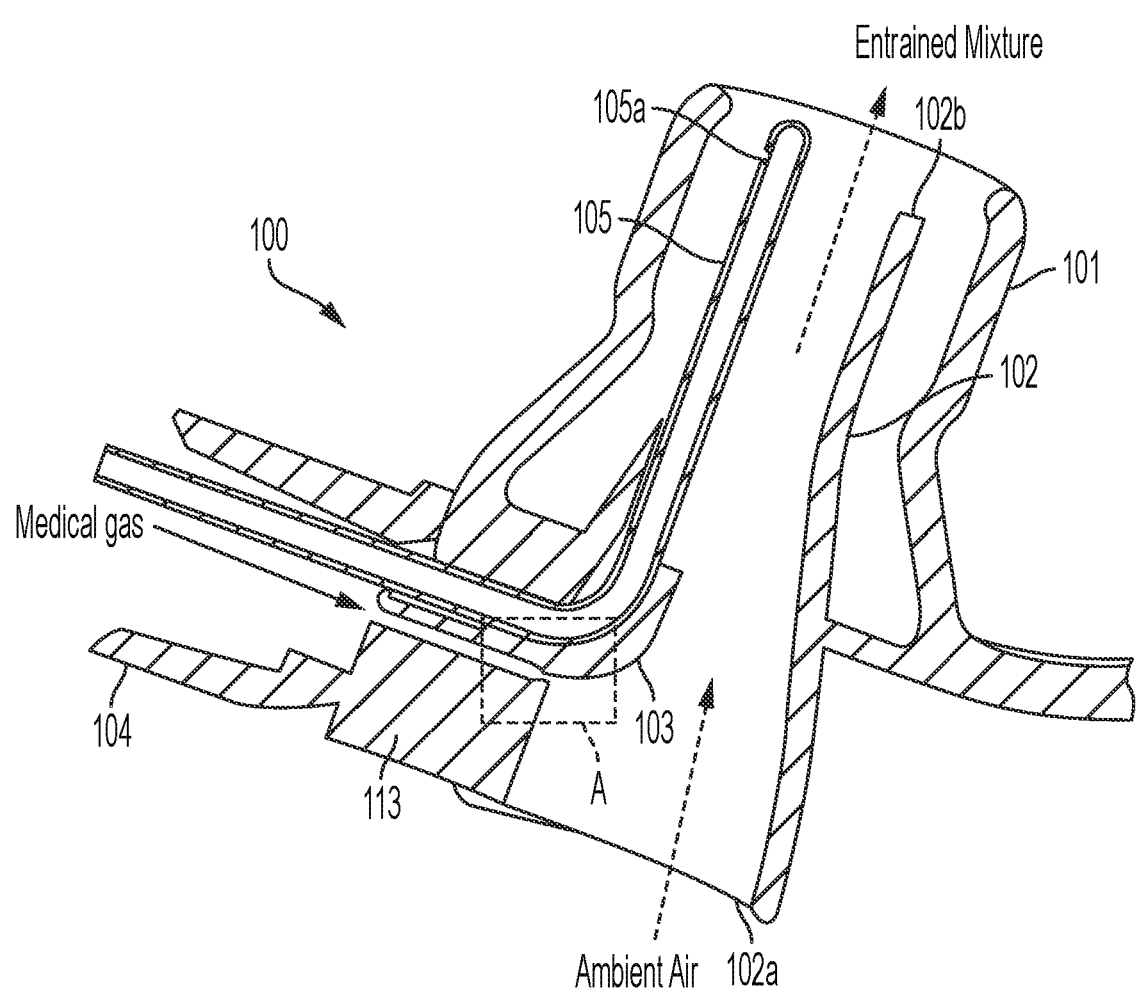
FIG. 1 illustrates a cross-sectional view of a portion of an example patient interface.

As used herein, the singular form of "a", "an", and "the" include plural references unless the context clearly dictates otherwise. As used herein, the statement that two or more parts or components are "coupled" shall mean that the parts are joined or operate together either directly or indirectly, e.g., through one or more intermediate parts or components, so long as a link occurs. As used herein, "operatively coupled" means that two or more elements are coupled to operate together or are in communication, unidirectional or bidirectional, with one another. As used herein, the term "number" shall mean one or an integer greater than one (i.e., a plurality). As used herein a "set" shall mean one or more.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

An embodiment employs a surface to adhere a pressurized jet of gas via the Coanda effect, permitting the jet of gas to be directed via employment of surface geometry as desired. Various embodiments therefore make use of the Coanda effect to entrain ambient air with a jet of medical gas for delivery via a patient interface.

The Bernoulli principle describes the relationship between fluid velocity and fluid pressure where increasing fluid velocity produces a reduction in fluid pressure. As such, when fluid flows (sometimes referred to as a jet) into an area of lower or zero velocity (sometimes referred to as ambient), it inherently has a lower pressure than the ambient and thus the ambient fluid is pulled toward the jet. This, plus the effects of shear-induced turbulent flux, cause the ambient fluid to be entrained into the jet flow.

When the jet of fluid enters the ambient fluid, an axisymmetric low pressure is formed around the jet and the resulting forces balance around the entire jet and produce a stable flow which propagates in a straight line, assuming no other outside forces are affecting it. If a boundary, such as a wall, is placed sufficiently close to the jet, then there is little or no ambient fluid to balance the low pressure formed around that portion of the jet and so the resulting unbalanced forces cause instability in the jet flow, which tends to pull the jet toward the boundary. The jet will remain attached to the boundary until the differential pressure is no longer sufficient to pull the jet toward the boundary. This is known as the Coanda effect and is described by the tendency of a fluid flow to be pulled toward and remain attached to a nearby boundary such as a wall.

The description now turns to the figures. The illustrated example embodiments will be best understood by reference to the figures. The following description is intended only by way of example, and simply illustrates certain example embodiments.

FIG. 1 illustrates in cross section a portion (one side) of a patient interface 100. In an embodiment, patient interface 100 is the mechanism that interfaces directly with the patient's air passage, e.g., nasal cavity. For example, patient interface 100 comprises an internal nasal pillow 101 that contains elastomeric feature(s) that aid in the interface contouring and sealing to the patient's airway. Patient interface 100 contains geometry such as conduit 102 and its entrainment 102a and nasal 102b openings that assists in entraining and/or increasing positive pressure along the downstream direction of patient interface 100. Patient interface 100 also contains features such as optional and/or removable skirts (730b, 731b of FIG. 7) for controlling sound or noise and flow or pressure of the gas passing through patient interface 100, while effectively extending the length of conduit 102 and defining an entrainment opening further upstream from the nasal opening, for example as illustrated in FIG. 2A, 230a, 202a. Patient interface 100 also contains rigid feature(s), such as surface 103 and frame 213a, that aid in interfacing with the other elements, such as skirts 730b, 731b, tubing 515, internal nasal pillow(s) 101, etc., to allow parts of patient interface 100 to be removed and replaced as needed to meet the requirements of a reimbursable mask.

It is noted that while patient interface 100 illustrated in FIG. 1 is formed with an internal nasal pillow 101 (i.e., seals to the inside of the nose), features of the embodiments may function in any other style of mask such as, but not limited to, a standard mask that seals on outside of the patient's nose, any nasal pillow interface, a nasal cushion, a nasal mask, a full-face mask, etc. Further, while internal nasal pillow 101 may be formed of an elastomeric material to facilitate patient comfort and sealing, other materials, e.g., rigid materials, may be used and the internal geometry of the patient's airway utilized to generate positive pressure as opposed to doing so via the material of patient interface 100.

As illustrated in FIG. 1, patient interface 100 includes an entrainment opening 102a and a nasal opening 102b defined by a conduit 102. The example embodiment of FIG. 1 includes a surface 103, here in a curved form, that extends from a chamber 106a (refer to FIG. 1A) that contains pressurized medical gas such as oxygen and curves into the conduit 102. Chamber 106a may be formed by a component, such as frame 113 having a port or interface 140, such as for attachment to tubing 515 (as further described herein).

As illustrated, surface 103 begins in chamber 106a and terminates in conduit 102 via a curve of about 90 degrees. Pressurized medical gas (indicated by dashed arrow in FIG. 1A) is provided through an orifice 107a, for example formed via sidewall(s) of chamber 106a and surface 103, as a high velocity jet, e.g., having a velocity of about 310 m/s. As further illustrated in FIG. 1A, orifice 107a is proximate to surface 103 as it extends onward into the interior of conduit 102. In an embodiment, an offset 108a between orifice 107a and an extended part of surface 103 (nearer to nasal end) is employed, as further described in connection with FIG. 3. In one example, orifice 107a may be sized to have a cross sectional area of about 0.1 mm to about 0.4 mm. In one example, the offset 108a may be sized about $5/1000^{th}$ to $20/1000^{th}$ inches. In one example, the sidewall(s) 109a may be sized about $8/1000^{th}$ to 0.1 inch tall.

The jet of gas adheres to, or follows closely above, surface 103 due to the Coanda effect. This permits the jet of gas to follow surface 103 into the conduit 102 in a guided manner. As will be further described herein, surface 103 may be provided with or proximate to one or more sidewalls, e.g., sidewall 109a of FIG. 1A, to further assist with guiding the jet of gas as desired.

In one example, jet of gas travels along or is adhered to surface 103 via the Coanda effect. This entrains ambient air, which is at a relative 0 Pa pressure near entrainment opening 102a absent a pulse of gas. When jet of gas is provided (at about 250 m/s), pressure drops within conduit 102 proximate to orifice (107a of FIG. 1A) to about −500 Pa and ambient air begins to move upward in conduit 102 (at about 8 m/s). As jet of gas entrains ambient air (refer to FIG. 3), pressure within a middle to upper part of conduit 102 rises to about 1470 Pa, while jet of gas slows to about 150 m/s. At nasal opening 102b, pressure of gas is about 1960 Pa, where jet of gas and ambient gas (entrainment mixture) move at about 40 m/s.

As shown in FIG. 1, a sensor or pressure sensing element 105 may be provided, for example an electric pressure sensor or a pressure sensing line with an opening or pressure sensing port 105a proximate to the nasal opening 102a of conduit. Such an arrangement provides for sensing, e.g., pressure proximate to the patient's nasal cavity. As depicted in FIG. 1, the sensor 105 may take the form of a tube that is angled about 90 degrees to run alongside or approximately parallel to medical gas delivery (initially) and entrained mixture delivery (near nasal end). As may be appreciated, sensor 105 may include other sensor(s) in addition to or in lieu of a pressure sensing line as illustrated in FIG. 1, as discussed in connection with the examples of FIG. 4.

Sensor 105 may be formed as a manometer-style tube that ports the pressure generated within nasal end 102b area of patient interface 100 into a secondary lumen (517 of FIG. 5) of a multi-lumen tube (515 of FIG. 5) for pressure measurement at an operatively coupled controller. Pressure measurement is necessary for closed-loop feedback to allow for the controller to monitor and adjust therapy pressure within the ISO standard, e.g., per a breathing or ventilation program. This is required, for example, to be considered a ventilator therapy.

One suitable configuration of sensor 105 is a stainless steel, thin-walled tube that has been bent or shaped (such as bent to have a 90-degree angle), capped, and side drilled to form an opening 105a to minimize the flow-induced impact on the static pressure reading. It is noted that opening may be at a terminal end of sensor 105 rather than a side location. Further, other materials may be used for sensor tubing, such as those described in connection with tubing 515.

Figure 2:
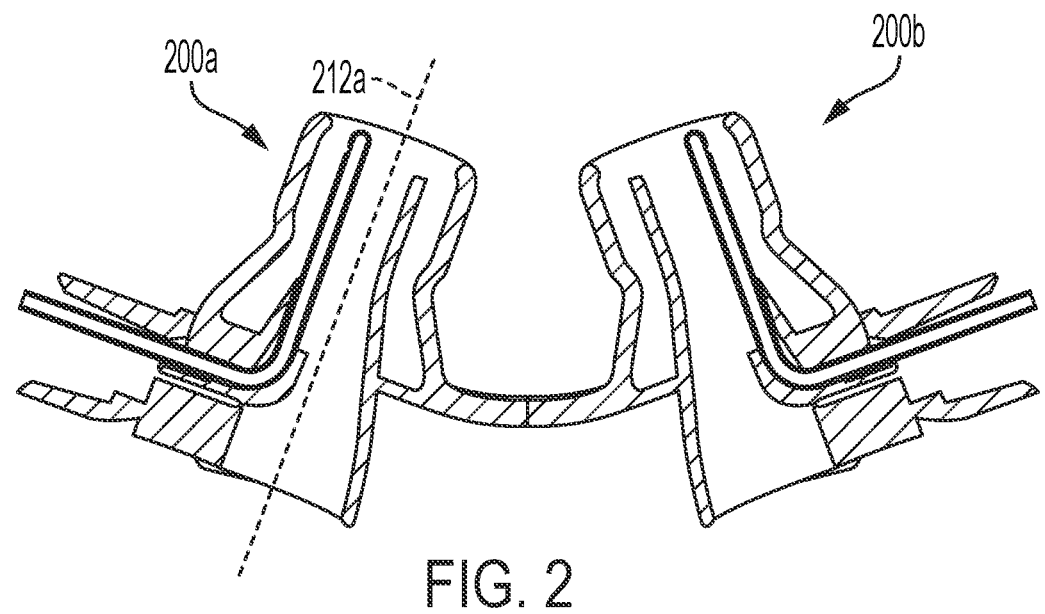
FIG. 2 illustrates a cross-sectional view of an example patient interface.
Figure 2A:
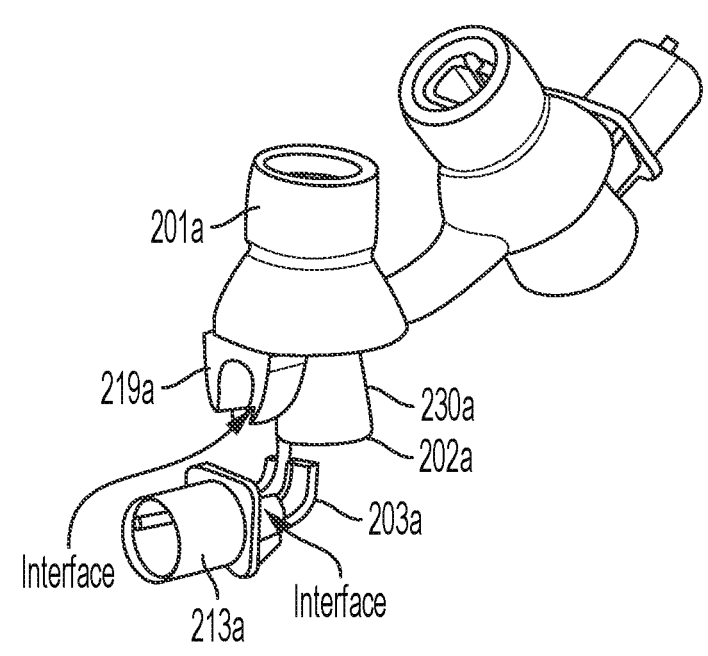
FIG. 2A illustrates an example patient interface in a partially exploded view.

FIG. 2 illustrates an example of a two-sided patient interface, i.e., one side for each nasal cavity. Here, a first side 200a and a second side 200b are joined together to form a nasal delivery interface for the patient. As illustrated in FIG. 1, side 200a may correspond to patient interface 100 of FIG. 1. The view of FIG. 2 illustrates a conduit axis 212a that runs substantially parallel to the flow direction of patient interface 100. For example, referring to FIG. 1, ambient air enters conduit 102 via entrainment end 102a and runs along the conduit axis 212a to exit the nasal end 102b.

FIG. 2A illustrates an example patient interface in a partially exploded view. In the view of FIG. 2A the left side (as illustrated) is in a partially exploded view to highlight that rigid component, frame 213a, interfaces with a clip interface 219a (which may also be a rigid component forming conduit). This permits frame 213a and surface 203a to be seated in conduit, which is covered in this view by internal nasal pillow 201a and skirt 230a. It is noted that because skirt 230a is included in this example, the length of conduit (entrainment opening 202a) is further upstream from the orifice delivering the jet of gas within conduit. FIG. 9 provides an unobstructed view of frame 213a (913), viewed from the orifice side, as further described herein.

Figure 1A:
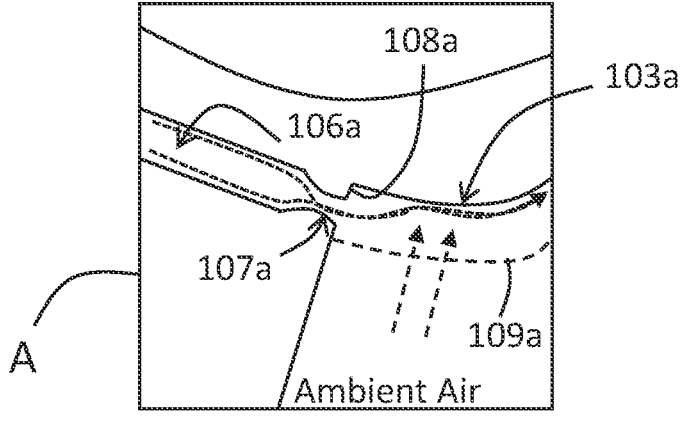
FIG. 1A illustrates panel A of FIG. 1.
Figure 3:
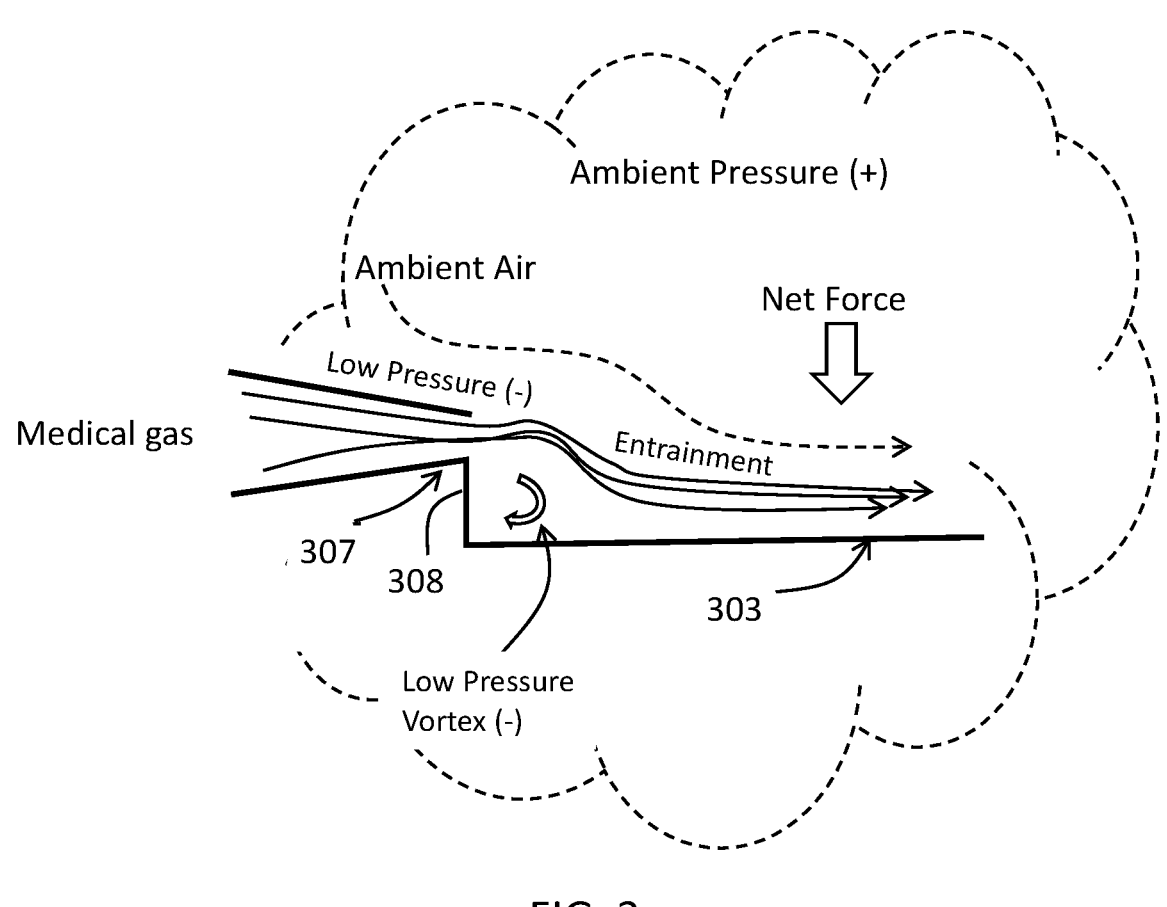
FIG. 3 illustrates an example view of airflow in an example patient interface.

Illustrated in FIG. 3 is a side view of surface 303, offset 308 and orifice 307 as referenced in connection with FIG. 1A. Here, a jet of fluid (illustrated as medical gas-solid arrows) enters the ambient air (dashed arrow), and an axisymmetric low pressure is formed around the jet. The resulting forces balance around the entire jet and produce a stable flow which propagates in a straight line. Here surface 303 is placed proximate to the opening 307 and therefore the jet is produced proximate to surface 303, dictated by offset 308 (which is optional). There is little or no ambient air between the surface 303 and the jet exiting opening 307 to balance the low pressure formed around that portion of the jet exposed to ambient air, e.g., within conduit 102 of FIG. 1, and the resulting unbalanced forces (net force in FIG. 3) cause instability in the jet flow which tends to pull the jet toward and adhere it to surface 303. The jet will remain attached to surface 303 and entrain ambient air to form an entrained mixture until the differential pressure is no longer sufficient to pull the jet toward surface 303. This is known as the Coanda effect and is described by the tendency of a fluid flow to be pulled toward and remain attached to a nearby boundary such as surface 303.

Patient interface 100 geometry described in connection with FIG. 1 contains a medical gas delivery orifice that is perpendicular to the direction of entrained flow, which is directed by curved surface 103; however, patient interface 100 may be configured with a variety of orifice angles with respect to the direction of entrained flow, for example in the range of greater than 0 degrees and less than 180 degrees relative to the direction of entrained flow.

Figure 4:
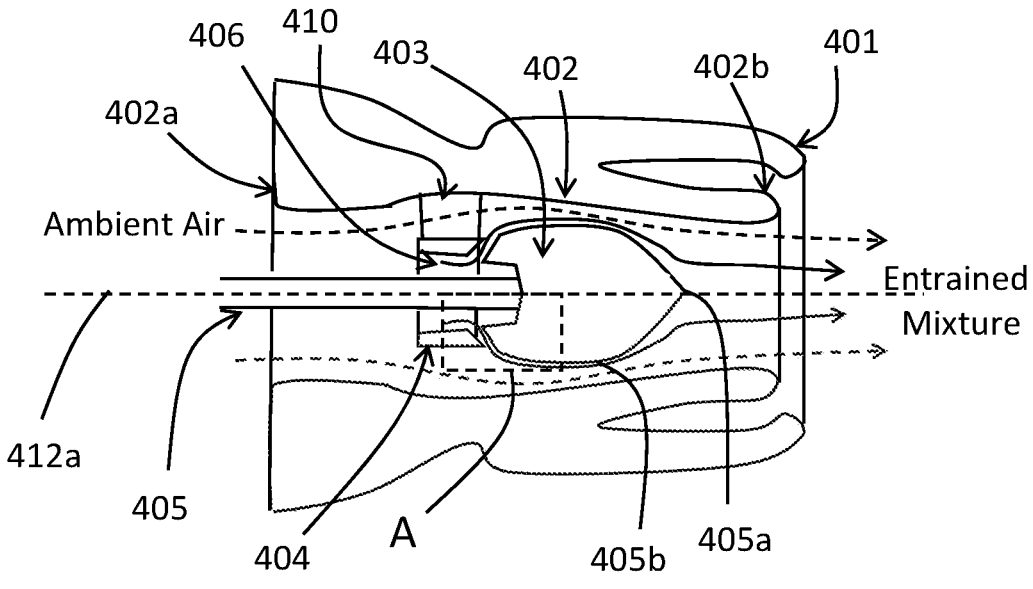
FIG. 4 illustrates a cross-sectional view of an example patient interface.
Figure 4A:
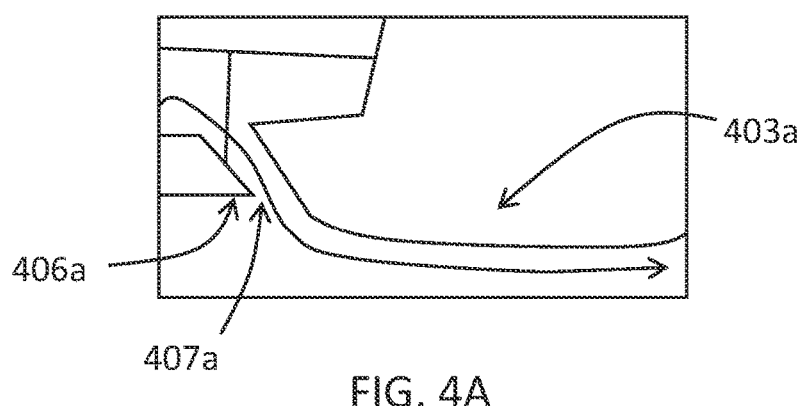
FIG. 4A illustrates panel A of FIG. 4.

By way of example, FIG. 4 illustrates one side, in cross-sectional view, of an embodiment in which surface 403 is provided by an at least partially circumferential element (circumferential in the sense that the surface extends relative to or surrounding the conduit axis). As indicated, surface 403 is enclosed within conduit 402 between entrainment opening 402a and nasal opening 402b. A port or interface 404 provides a supply of pressurized medical gas (solid arrows) within chamber 406. Chamber 406 coordinates with surface 403 to form opening(s), one of which is illustrated in FIG. 4A at 407a. As described herein, one or more supports 410 may attach to one or more of the port or interface 404 and the circumferential element providing surface 403, as further described in connection with FIG. 4A-C.

As shown in FIG. 4, nasal pillow 401 encloses conduit 402 at the nasal end, whereas ambient air (dashed arrows) is entrained from ambient end. In the example illustrated in FIG. 4, sensor 405 (pressure sensing line) extends linearly through conduit 402 to position sensor opening (or pressure sensing port) 405a proximate to nasal end of conduit 402 such that it is oriented to face parallel to the flow. In an embodiment, as illustrated in FIG. 4 and FIG. 4D, sensor opening 405a may be alternatively or additionally provided at one or more different areas, for example at a surface of one or more supports 410d or element providing surface 403d, as indicated at 405b. In an alternative embodiment, a pressure sensing element in the form of an electric pressure sensor (e.g., a transducer, resistive, capacitive, piezoelectric, optical, or MEMS sensor) may be used in one or more of the aforementioned locations as the sensor 405, the electric sensor being electrically coupled (e.g., via wiring through tubing 515 or secondary lumen 517, shown in FIG. 5 discussed below) to a remotely located unit such as a microcontroller or communication element operatively coupled thereto. This embodiment has an advantage of reducing time delay associated with pneumatic pressure sensing, i.e., there is no time delay between a change of the pressure at the sensor location and the determination of the pressure via the sensor 405. In case of a pressure sensing line as sensor 405 with sensor opening 405a there could be a delay around 100 milliseconds. As with the arrangement of FIG. 1, a conduit axis 412a is illustrated in FIG. 4.

As can be appreciated in the detailed view of FIG. 4A, in an embodiment having a circumferential element that provides surface 403, an orifice 407a is formed via cooperation between surface 403a and wall of chamber 406a. This permits a pressurized jet of medical gas to be expelled from orifice 407a where it again is adhered to surface 403a via the Coanda effect. As illustrated in FIG. 4, this permits entrainment of ambient air with the jet of gas to form an entrained mixture comprising the ambient air and medical gas, supplied to the patient via nasal end 402b.

By way of example, in the arrangement of FIG. 4, ambient air at about 0 Pa (absent a pulse of medical gas) is thereafter entrained by a jet of gas adhered to surface 403 and exits the nasal end at about 1960 Pa as an entrainment mixture, similar to that described in connection with FIG. 1. The pressure gradient within an embodiment configured as in FIG. 4 is approximately −10 Pa at ambient or entrainment end, about −1000 Pa near opening 407a (−1500 Pa on surface 403), and rises to about 320 Pa about halfway between opening 407a and nasal end before exiting at about 1960 Pa. Similar to the flow speeds described in connection with FIG. 1, ambient air is entrained by a pulse of gas at about 10 m/s at entrainment end, increases to about 100 m/s near opening 407a, which expels gas at about 210 m/s. The entrainment mixture slows to about 35 m/s about halfway between opening 407a and nasal end 402b before exiting at about 30 m/s.

Figure 4B:
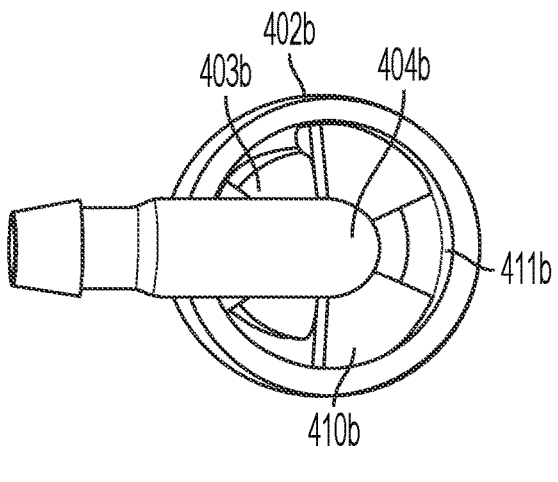
FIG. 4B illustrates an entrainment end view of a portion of an example patient interface.

A view of the entrainment end 402a of an embodiment as depicted in FIG. 4 is provided in FIG. 4B. Here it can be understood that a circumferential element may include an interface or port 404b that is supported by one or more supports or suspension elements 410b that attach to or extend from the interior wall 411b of conduit 402 to suspend the circumferential element, including surface 403, in the middle or interior of conduit 402. As may be appreciated, fluid connectivity, e.g., to a supply of pressurized medical gas, may be provided via one or more supports 410b or via interface or port 404b, which in turn may attach to tubing (not illustrated in FIG. 4B, refer to FIG. 5 at 515).

Figure 4C:
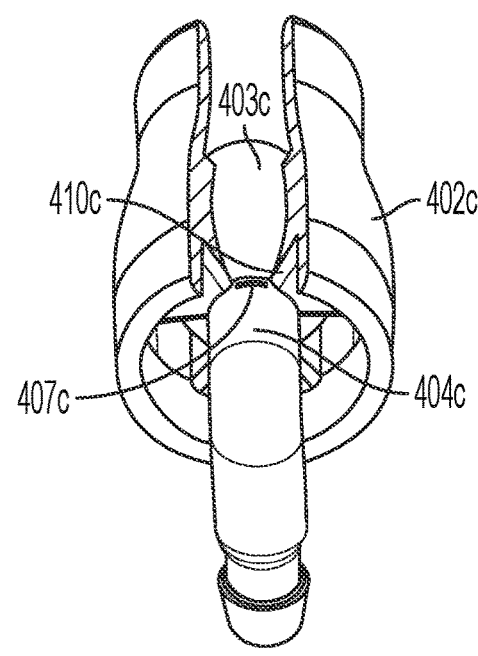
FIG. 4C illustrates a partial cross-sectional view in perspective of the example patient interface of FIG. 4 and FIG. 4B.
Figure 4D:
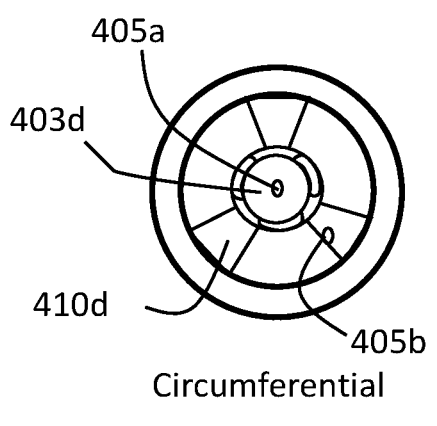
FIG. 4D illustrates an example front view of the patient interface of FIG. 4.

FIG. 4C illustrates a partial cross-sectional view in perspective of the example patient interface of FIG. 4 and FIG. 4B. Here, the surface 403c formed via circumferential element is illustrated with part of the conduit 402c removed for illustration purposes. The interface or port 404c provides influx of pressurized medical gas for delivery via orifices (one of which is indicated at 407c) to the patient via the Coanda effect (adhering to surface 403c). Supports, one of which is indicated at 410c, are illustrated, which may attach to interface or port 404c and/or circumferential element providing surface 403c.

Figure 5:
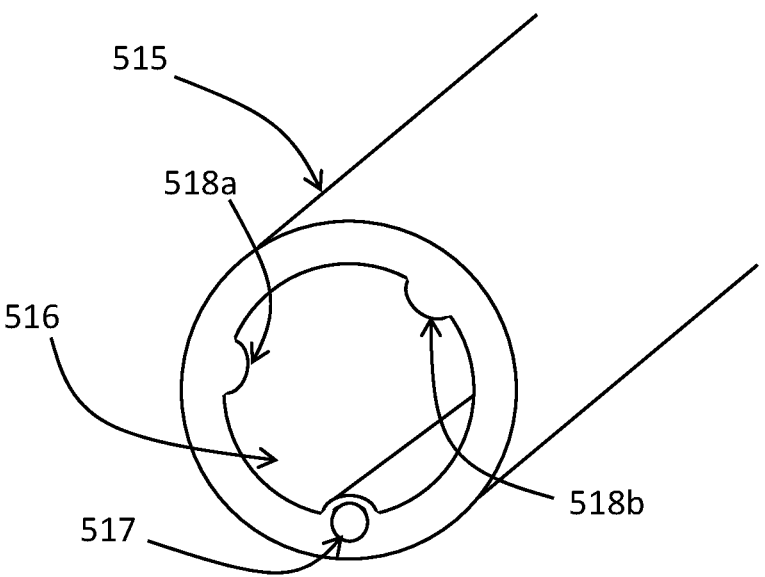
FIG. 5 illustrates example tubing.

FIG. 5 provides an example view of an embodiment's tubing 515, which may be connected to or extend from a port or interface, e.g., port or interface 104 or 404 of FIG. 1 and FIG. 4, respectively, to supply pressurized medical gas. Tubing 515 may include a primary or main lumen 516 that provides a supply of pressurized medical gas, e.g., to chamber 106a, 406 as shown in FIG. 1 and FIG. 4, respectively. Tubing 515 may also include a secondary lumen 517 for carrying another element such as distal end of sensor 105 of FIG. 1, another gas type, such as a secondary medical gas, or a combination of the foregoing. In some examples, tubing 515 may contain additional lumens, e.g., for carrying multiple types of medical gas such as air, oxygen, nitrous oxide, etc. or delivery of medicine. Tubing 515 may also be formed with a single, primary lumen 516. Tubing 515 is illustrated containing no additional components; however, tubing 515 may comprise co-extruded components such as wires for sensors, sensors, radioscopic elements (e.g., barium sulfate), tube reinforcements (spiral wire, braids, etc.), or combinations of the foregoing.

In the example of FIG. 5, tubing 515 includes anti-occlusion ribs 518a, 518b, spaced approximately equidistant from one another and secondary lumen 517. In one example, an embodiment includes part of a sensor such as sensor 105 in secondary lumen 517 such that it may extend back through patient interface 100 and transmit readings to a remotely located unit such as a microcontroller or communication element operatively coupled thereto.

Tubing 515 may be formed as an elastomeric tubing that contains at least two lumens 516, 517 that are separated by a septum. In one example, one lumen 516 is used to deliver the pressurized medical gas to the Coanda surface, e.g., surface 103, and one lumen 517 is used to provide a pressure sensor, e.g., sensor 105, that senses pressure being generated in nasal end 102b of patient interface 100. The sensed pressure may be fluidly communicated back to a controller for measurement and response. As described herein, tubing 515 optionally contains features such as anti-occlusion ribs 518a, 518b within the lumen(s) 516, 517 to prevent full occlusion thereof, for example if tubing 515 were to become kinked.

The material selected for this tubing may comprise Lubrizol TECOFLEX EG-80A. TECOFLEX EG-80A has an ultimate tensile strength of about four times that of silicone, which allows for thinner walled tubing compared to silicone while still being able to withstand the internal pressure of the medical gas in main lumen 516. The thinner wall tubing 515 combined with the relatively soft durometer (72A nominal for EG-80A) provides tubing 515 with a softer and more flexible feeling compared to equivalent performance silicone or PVC tubing. TECOFLEX EG-80A is a medical grade thermoplastic polyurethane (TPU) that has been tested to and passed ISO10993-4 (Hemolysis), ISO10993-5 (Cytotoxicity), ISO10993-6 (Intramuscular Implantation, 2-week and 13-week), ISO10993-10 (Intracutaneous Injection), and ISO10993-11 (Systemic Injection). TECOFLEX is a registered trademark of Lubrizol Advanced Materials, Inc. in the United States and/or other countries.

Arkema PEBAX 2533 SA 01 MED may also be used for tubing 515. Like TECOFLEX EG-80A, PEBAX 2533 SA 01 MED has an ultimate tensile strength of about five times that of silicone, which allows for thinner walled tubing compared to silicone while still being able to withstand the internal pressure of the medical gas in the main lumen 515. Thinner wall tubing 515 combined with the relatively soft durometer (77A nominal for PEBAX 2533 SA 01 MED) provides tubing 515 with a softer and more flexible feeling compared to equivalent performance silicone or PVC tubing. PEBAX 2533 SA 01 MED is a medical grade TPU that has been tested to and passed U.S. Pharmacopeia (USP) Class VI (Systemic toxicity, skin irritation, and infection). PEBAX is a registered trademark of Arkema France Corporation in the United States and/or other countries.

Although certain materials have been described as suitable for use with tubing 515, it should be noted that several other medical-grade elastomers such as, but not limited to, silicone, polyvinyl chloride (PVC), thermoplastic elastomer (TPE), etc., may be utilized.

Figure 6:
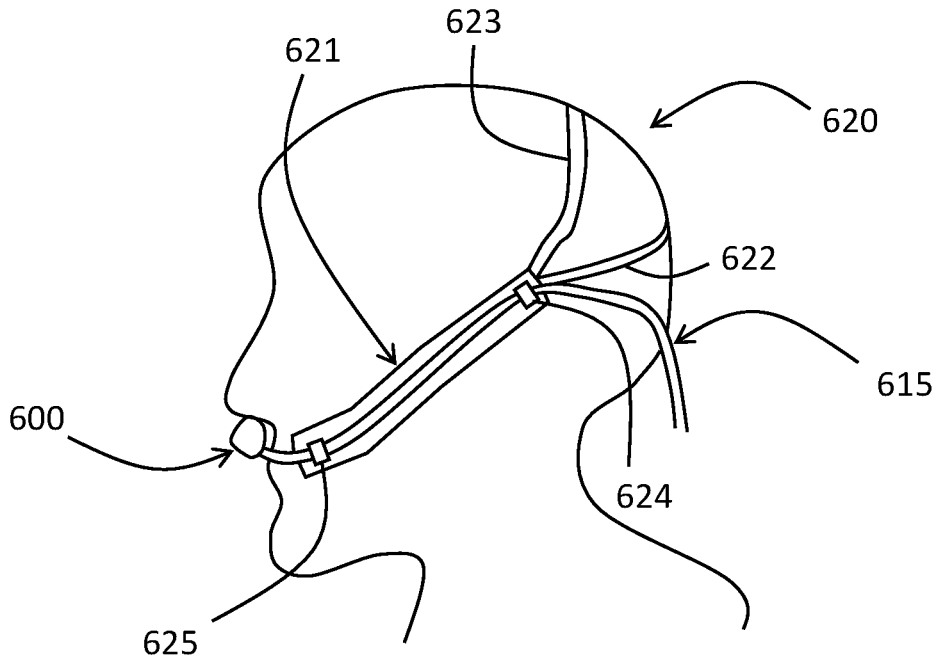
FIG. 6 illustrates an example system.

A system is illustrated in FIG. 6 that includes a patient interface device 600 along with headgear element(s) (collectively indicated at 620), which may be removable from patient interface 600 or statically connected thereto. In one example, headgear 620 includes one or more straps 621, 622, 623 that secure patient interface 600 proximate to the nasal cavity of a patient. One or more clips 624, 625 may be provided to secure tubing 614 into a desired position.

In the example of FIG. 6, a main strap 621 includes a backing or padding for patient comfort. In one example, main strap 621 may bifurcate to form two straps 622, 623 that further secure patient interface 600 to patient.

In an embodiment, headgear 620 is a strap 621 that connects to and secures patient interface 600 in place on the patient. Strap 621 may comprise a fabric strap with at least two separate loops or elements 623, 623 to meet the requirements of a reimbursable mask. Strap 621 includes connection features such as clips 624, 625 that securely clip to tubing 615 while also allowing for fitment adjustment on the patient. In one example, headgear 620 includes clip(s) 624 toward the rear to the headgear that align tubing 615 along a band or wider portion of strap 621 of headgear 620 and raises tubing 615 off the patient's ear for improved comfort during use. Headgear 620 may be detachable and replaceable, e.g., from patient interface 600, to satisfy the requirements of a reimbursable mask.

In an embodiment, patient interface 100 contains rigid or elastomeric features that wrap around surface 103 in the form of a skirt in order to improve entrainment and/or pressure generation, and/or decrease sound pressure levels of interface patient interface 100. However, patient interface 100 could function with no skirt, a partial skirt, partially enclosed, or fully enclosed configuration.

Figures 7A, 7B, 8A, 8B, 8C:
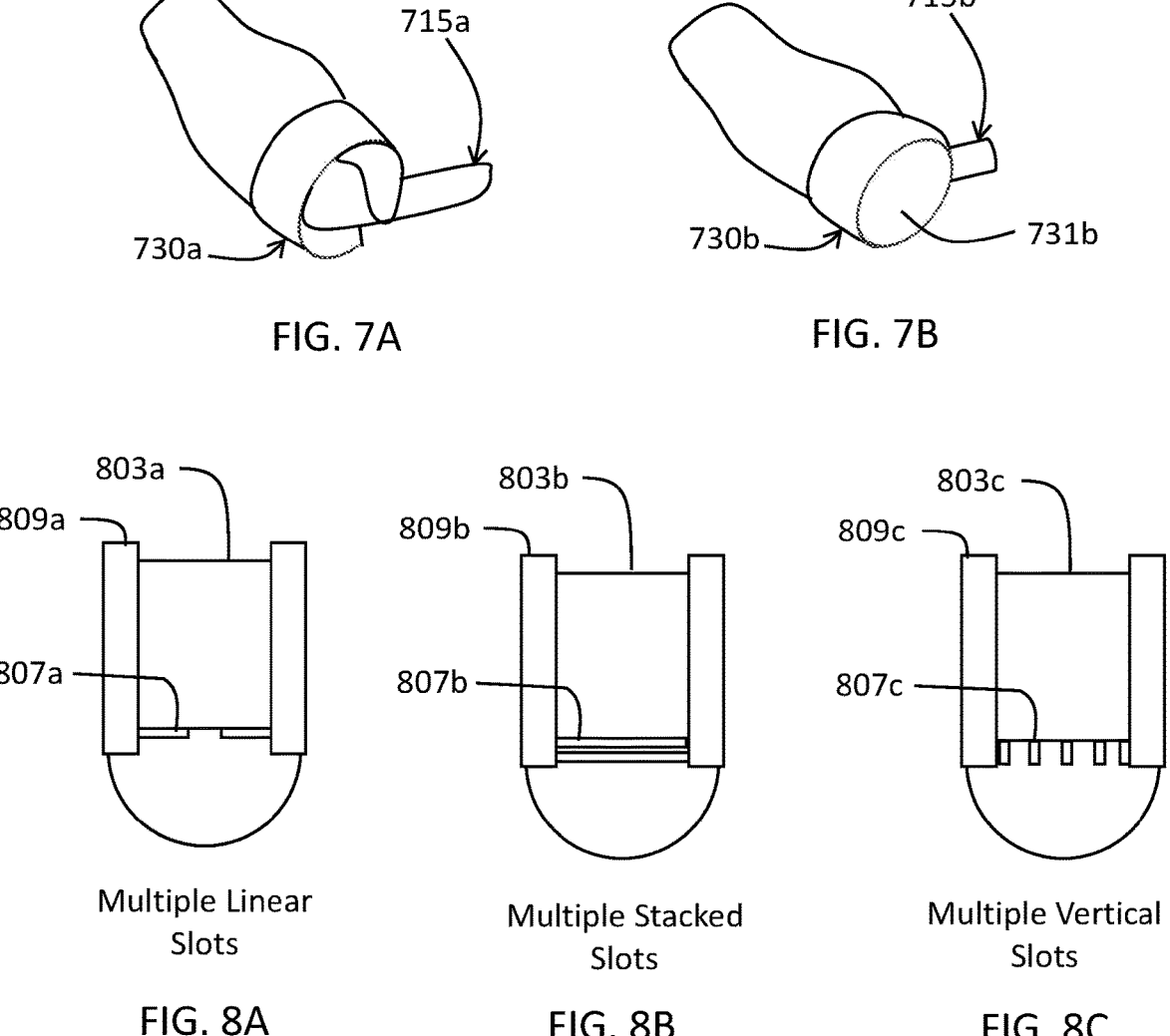
FIG. 7(A-B) illustrates examples of patient interface skirts.
FIG. 8(A-H) illustrates example orifice arrangements.

By way of example, illustrated in FIG. 7A and FIG. 7B are examples of removable skirts that may be used in connection with patient interface 100, 200a, 200b, or the like. In one embodiment, no skirt is provided. However, in another embodiment a skirt 730a is provided that partially encloses entrainment opening of conduit proximate to tubing 715a. In another embodiment, a skirt 731b is provided to fully enclose the entrainment side of patient interface proximate to tubing 715b. As may be appreciated, either of skirt 730a and 731b may be placed onto a patient interface at the ambient side opening and removed therefrom, e.g., to modulate noise associated with operation of patient interface, which may be quite loud (e.g., about 80 dB) without any sound buffering components.

FIG. 8A through FIG. 8H illustrate various examples of orifices 807a-h that may be formed to provide a jet of gas proximate to a surface to use the Coanda effect, as described herein. In the example of FIG. 8A, two linear slots (one of which is indicated at 807a) may be provided to produce a jet of gas that adheres to the surface 803a, with guidance from sidewalls (one of which is indicated at 809a).

In the example of FIG. 8B, multiple stacked slots, e.g., two as shown (one of which is indicated at 807b) may be provided to produce a jet of gas that adheres to the surface 803b, with guidance from sidewalls (one of which is indicated at 809b).

In the example of FIG. 8C, multiple vertical slots as shown (one of which is indicated at 807c) may be provided to produce a jet of gas that adheres to the surface 803c, with guidance from sidewalls (one of which is indicated at 809c).

In the example of FIG. 8D, linear orifices (one of which is indicated at 807d) may be provided to produce a jet of gas that adheres to the surface 803d, with guidance from sidewalls (one of which is indicated at 809d).

In the example of FIG. 8E, stacked orifices (one of which is indicated at 807e) may be provided to produce a jet of gas that adheres to the surface 803e, with guidance from sidewalls (one of which is indicated at 809e).

In the example of FIG. 8F, a non-linear slot 807f may be provided to produce a jet of gas that adheres to the surface 803f, with guidance from sidewalls (one of which is indicated at 809f).

In the example of FIG. 8G, a non-uniform section 807g may be provided to produce a jet of gas that adheres to the surface 803g, with guidance from sidewalls (one of which is indicated at 809g).

In the example of FIG. 8H, multiple direction orifices as shown (one of which is indicated at 807h) may be provided to produce a jet of gas that adheres to the surface 803h, with guidance from sidewalls (one of which is indicated at 809h).

As described herein, one or more sidewalls 109a may be included to assist with guidance of the jet of gas along surface 103 but are not required. As shown in FIG. 9, surface 903 extends from frame 913 and curves in one example about 90 degrees as it enters the conduit (not illustrated in FIG. 9). One or more sidewalls, one of which is illustrated at 909, assist in guiding the jet of gas along surface 903 as it exits orifice 907 from supply via tubing 915. It is noted that in an embodiment, the curvature of the surface may include other angles, such as between 0 and 180 degrees (greater than 0 degrees and less than 180 degrees). In one example, the curvature may be between 45 and 100 degrees.

Surface 903 may be a rigid component that interfaces with tubing 915. Medical gas delivery orifice(s) 907 provide the pressurized medical gas to the conduit via surface 903, which may be non-linear, that in turn influences the direction of the pressurized medical gas in through the Coanda effect. The example illustrated in FIG. 9 also contains two sidewalls, one of which is indicated at 909, to aid in maintaining and guiding the Coanda effect. The element may also contain an offset between orifice 907 and surface 903 to improve the initial generation of the Coanda effect via vortex, as illustrated in FIG. 3. An offset may also be provided between orifice 907 and an outer edge of sidewall 909 to aid in maintaining and guiding the Coanda effect.

Varying the orifices, as described in connection with FIG. 8A through FIG. 8H, may provide different levels of entrainment of ambient air, different noise levels, etc., depending on the configuration chosen and the other patient interface elements present (such as skirts 730a, 731b). In addition, as shown in FIG. 10 A-D, different sidewall configurations may be utilized. For example, shown in FIG. 10A is a parallel configuration where two sidewalls are divided by an intervening sidewall 1009a, providing two surfaces, one of which is indicated at 1003a and two orifices, one of which is indicated at 1007a.

In the example of FIG. 10B, a convergent configuration in which two sidewalls are divided by a converging, intervening sidewall 1009b, provides two converging surfaces, one of which is indicated at 1003b and two orifices, one of which is indicated at 1007b.

In the example of FIG. 10C, a divergent configuration in which two sidewalls are divided by a diverging, intervening sidewall 1009c, provides two diverging surfaces, one of which is indicated at 1003c and two orifices, one of which is indicated at 1007c.

In the example of FIG. 10D, a separated configuration in which two surfaces, one of which is indicated at 1003d and two orifices, one of which is indicated at 1007d, are separated by two intervening sidewalls, one of which is indicated at 1009d.

Referring to FIGS. 4 and 4C, in an example where a circumferential element is used to provide surface 403c, supports 410c may suspend or attached the element containing the surface 403c. In one example, one or more supports 410c attach to a circumferential element having surface 403c at or near orifice 407c and extend towards nasal opening of conduit 402c. As shown in FIG. 10E, which is a nasal end view of a patient interface having a circumferential character, one or more orifices 1007e may be provided in a circumferential manner about surface 1003e. Here, the device is configured such that surface 1003e and port or interface 1004e cooperate to form orifices 1007e in a circumferential manner. As described in connection with FIG. 8A through FIG. 8H, the one or more orifices 1007e may take a variety of forms, including those illustrated in FIG. 8A through FIG. 8H. Similarly, one or more orifices 1007e may be placed proximate to one or more sidewalls, for example as shown in FIG. 10A through FIG. 10D, when used in a configuration such as illustrated in FIG. 4.

Figure 11:
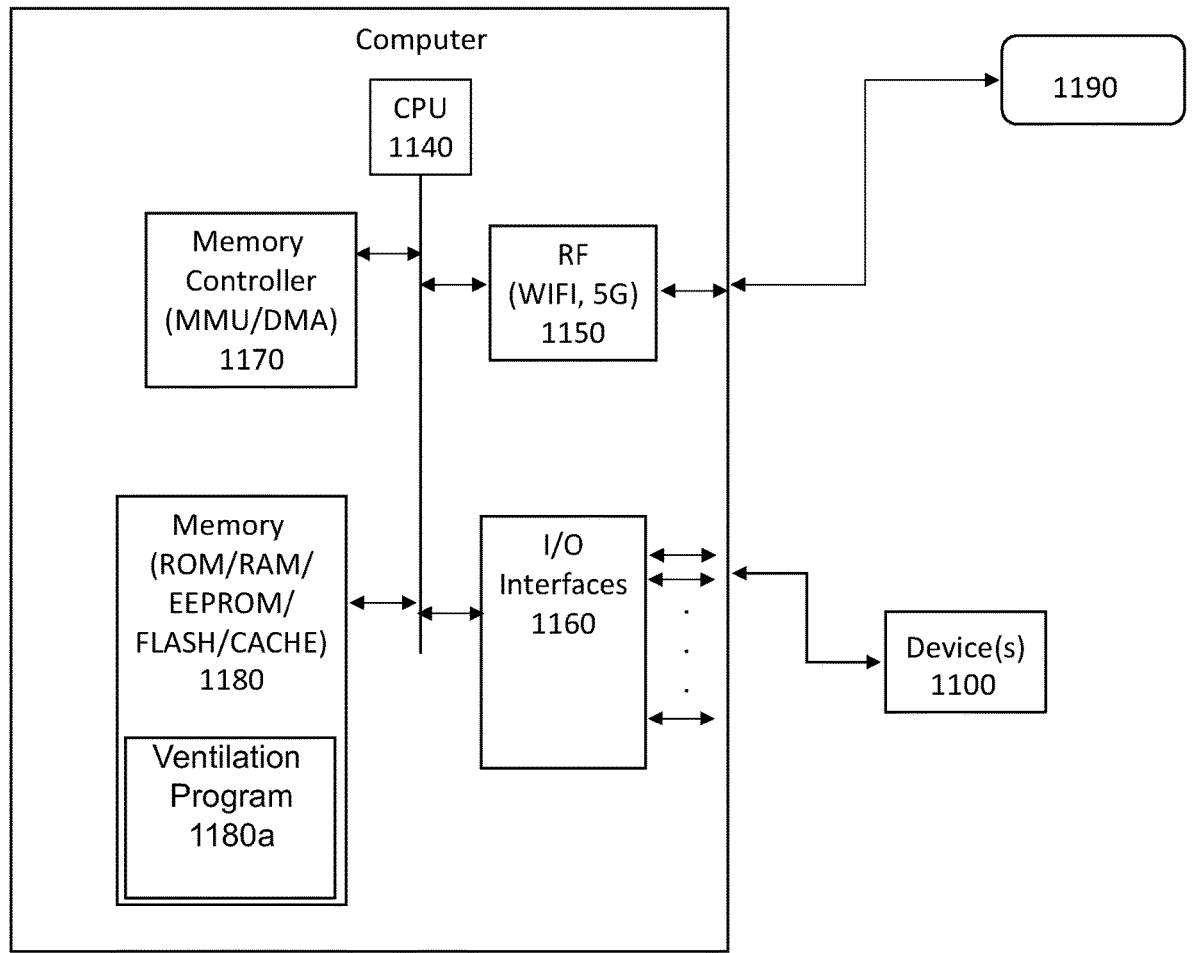
FIG. 11 illustrates a diagram of example system components.

Referring to FIG. 11, it will be readily understood that certain embodiments may include a controller or microcontroller for use in delivering pulses of medical gas from a source of medical gas 1190 via a patient interface 1100, coordinated with sensor data feedback, for example provided by sensor 105 included in patient interface 1100. In FIG. 11 an example of a computer and its components is illustrated, which may be used in a controller device for implementing certain of the functions or acts described herein, e.g., supplying timed pulses of medical gas. In addition, circuitry other than that illustrated in FIG. 11 may be utilized in one or more embodiments. The example of FIG. 11 includes certain functional blocks, as illustrated, which may be integrated onto a single semiconductor chip to meet specific application requirements.

One or more processing units are provided, which may include a central processing unit (CPU) 1140, which includes an arithmetic logic unit (ALU) that performs arithmetic and logic operations, instruction decoder that decodes instructions and provides information to a timing and control unit, as well as registers for temporary data storage. CPU 1140 may comprise a single integrated circuit comprising several units, the design and arrangement of which vary according to the architecture chosen.

Computer also includes a memory controller 1170, e.g., comprising a direct memory access (DMA) controller to transfer data between memory 1180 and hardware peripherals. Memory controller 1170 includes a memory management unit (MMU) that functions to handle cache control, memory protection, and virtual memory. Computer may include controllers for communication using various communication protocols (e.g., I$^2$C, USB, etc.).

Memory 1180 may include a variety of memory types, volatile and nonvolatile, e.g., read only memory (ROM), random access memory (RAM), electrically erasable programmable read only memory (EEPROM), Flash memory, and cache memory. Memory 1180 may include embedded programs, code and downloaded software, e.g., a breathing or ventilation program 1180a for delivering medical gas via a patient interface 1100 as described herein. By way of example, and not limitation, memory 1180 may also include an operating system, application programs, other program modules, code, and program data, which may be downloaded, updated, or modified via remote devices.

A system bus permits communication between various components of the computer. I/O interfaces 1160 and radio frequency (RF) devices 1150, e.g., WIFI and telecommunication radios, may be included to permit computer to send and receive data to and from remote devices using wireless mechanisms, noting that data exchange interfaces for wired data exchange may be utilized. Computer may operate in a networked or distributed environment using logical connections to one or more other remote computers or databases. The logical connections may include a network, such local area network (LAN) or a wide area network (WAN) but may also include other networks/buses. For example, computer may communicate data with and between sensor device(s) of patient interface 1100 collecting sensor data.

Computer may therefore execute program instructions or code configured to obtain, store, and analyze sensor data and perform other functionality of the embodiments, as described herein. A user can interface with (for example, enter commands and information) the computer through input devices, which may be connected to I/O interfaces 1160. A display or other type of device may be connected to the computer 500 via an interface selected from I/O interfaces 1160.

It should be noted that the various functions described herein may be implemented using instructions or code stored on a memory, e.g., memory 1180, that are transmitted to and executed by a processor, e.g., CPU 1140. Computer includes one or more storage devices that persistently store programs and other data. A storage device, as used herein, is a non-transitory computer readable storage medium. Some examples of a non-transitory storage device or computer readable storage medium include, but are not limited to, storage integral to computer, such as memory 1180, a hard disk or a solid-state drive, and removable storage, such as an optical disc or a memory stick.

Program code stored in a memory or storage device may be transmitted using any appropriate transmission medium, including but not limited to wireless, wireline, optical fiber cable, RF, or any suitable combination of the foregoing.

Program code for carrying out operations according to various embodiments may be written in any combination of one or more programming languages. The program code may execute entirely on a single device, partly on a single device, as a stand-alone software package, partly on single device and partly on another device, or entirely on the other device. In an embodiment, program code may be stored in a non-transitory medium and executed by a processor to implement functions or acts specified herein. In some cases, the devices referenced herein may be connected through any type of connection or network, including a local area network (LAN) or a wide area network (WAN), or the connection may be made through other devices (for example, through the Internet using an Internet Service Provider), through wireless connections or through a hard wire connection, such as over a USB connection.

Referring to FIG. 12, an embodiment includes a method of providing a patient interface as shown and described. In one example, a method comprises providing (1201) a conduit having an entrainment opening and a nasal opening disposed along a conduit axis. The method includes supplying (1202) a pressure sensing line having a pressure sensing port proximate to the nasal opening and configuring (1203) one or more orifices proximate to the entrainment opening to expel a jet of gas. The method further includes providing (1204) one or more surfaces having a first end and a second end, the first end being proximate to the one or more orifices and configured to direct a flow of the jet of gas expelled from the one or more orifices, the second end being closer to the nasal opening than the first end. As illustrated, the orifice and the surface are arranged to adhere (1205), in an operational state, the jet of gas to the surface via Coanda effect, thereby entraining ambient air into the entrainment opening to deliver the jet of gas and the ambient air through the nasal opening of the conduit.

Other embodiments may include a method of using a patient interface as shown and described, e.g., according to a breathing or ventilation program 1180*a*.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination. The word "about" or similar relative term as applied to numbers includes ordinary (conventional) rounding of the number with a fixed base such as 5 or 10.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system, comprising:
a headgear element;
a non-invasive ventilation patient interface detachably coupled to the headgear element and comprising:
a conduit disposed about a longitudinal axis, the conduit defining an entrainment opening and a nasal opening at opposing ends of the conduit such that the longitudinal axis passes through both the entrainment opening and the nasal opening;
a pressure sensing element proximate to the nasal opening;
one or more orifices proximate to the entrainment opening and configured to expel a jet of gas; and
one or more surfaces having a first end and a second end, the first end being proximate to the one or more orifices and directing a flow of the jet of gas expelled from the one or more orifices, the second end being closer to the nasal opening than the first end;
wherein, in an operational state, the jet of gas adheres to the one or more surfaces via the Coanda effect, thereby entraining ambient air into the entrainment opening to deliver the jet of gas and the ambient air through the nasal opening of the conduit.

2. The system of claim 1, comprising one or more suspension elements; wherein the one or more suspension elements suspend the one or more surfaces within the conduit via.

3. The system of claim 1, wherein:
the one or more surfaces extend circumferentially relative to the longitudinal axis, at least partially surrounding the longitudinal axis; and
the one or more orifices comprise a plurality of orifices disposed circumferentially about the longitudinal axis proximate to the first end of the one or more surfaces.

4. The system of claim 1, wherein the non-invasive ventilation patient interface further comprises a dual lumen having a primary lumen and a secondary lumen;
wherein the primary lumen is configured to deliver gas to the one or more orifices; and wherein the pressure sensing element comprises a pressure sensing line having an opening, the secondary lumen comprising at least a portion of the pressure sensing line.

5. The system of claim 4, wherein the opening of the pressure sensing line is disposed proximate to an end of the secondary lumen, the opening of the pressure sensing line being substantially orthogonal to the conduit axis.

6. The method of claim 4, wherein the secondary lumen runs parallel to the primary lumen.

7. The system of claim 1, wherein the one or more orifices and the first end of the one or more surfaces are laterally offset.

8. The system of claim 2, wherein one or more of the one or more surfaces is bounded on each side by the one or more suspension elements to control the jet of gas along the one or more surfaces.

9. The system of claim 1, wherein the one or more orifices comprises a predetermined opening shape selected from: one or more linear slots, multiple stacked slots, multiple vertical slots, one or more linear orifices, multiple stacked orifices, one or more non-linear slots, a non-uniform section, and multiple direction openings.

10. A system, comprising:
a headgear means;
a non-invasive ventilation patient interface means detachably coupled to the headgear means and comprising:
a conduit means disposed about a longitudinal axis, the conduit means defining an entrainment opening and a nasal opening at opposing ends of the conduit means such that the longitudinal axis passes through both the entrainment opening and the nasal opening;
a pressure sensing means proximate to the nasal opening;
one or more orifices means proximate to the entrainment opening and configured to expel a jet of gas; and one or more surface means having a first end and a second end, the first end being proximate to the one or more orifice means and directing a flow of the jet of gas expelled from the one or more orifice means, the second end being closer to the nasal opening than the first end;

wherein, in an operational state, the jet of gas adheres to the one or more surface means via the Coanda effect, thereby entraining ambient air into the entrainment opening to deliver the jet of gas and the ambient air through the nasal opening of the conduit means.

11. System of claim 10, comprising a suspension means;

wherein the one or more surface means is suspended within the conduit means via the suspension means.

12. The system of claim 10, wherein:

the one or more surface means extend circumferentially relative to the longitudinal axis, at least partially surrounding the longitudinal axis; and the one or more orifice means comprise a plurality of orifices disposed circumferentially about the longitudinal axis proximate to the first end of the one or more surface means.

13. The system of claim 10, comprising a lumen means having a primary lumen and a secondary lumen;

wherein the primary lumen is configured to deliver gas to the one or more orifice means; and wherein the secondary lumen comprises the pressure sensing means.

14. The system of claim 13, wherein the pressures sensing means comprises a pressure sensing port disposed proximate to an end of the secondary lumen, the pressure sensing port being substantially orthogonal to the longitudinal axis.

15. A method, comprising:

providing a conduit disposed about a longitudinal axis, the conduit defining an entrainment opening and a nasal opening at opposing ends of the conduit such that the longitudinal axis passes through both the entrainment opening and the nasal opening;

supplying a pressure sensing element proximate to the nasal opening;

configuring one or more orifices proximate to the entrainment opening to expel a jet of gas; and providing one or more surfaces having a first end and a second end, the first end being proximate to the one or more orifices and configured to direct a flow of the jet of gas expelled from the one or more orifices, the second end being closer to the nasal opening than the first end;

wherein the one or more orifices and the one or more surfaces are arranged to adhere, in an operational state, the jet of gas to the one or more surfaces via the Coanda effect, thereby entraining ambient air into the entrainment opening to deliver the jet of gas and the ambient air through the nasal opening of the conduit.

* * * * *